(12) United States Patent
Honda

(10) Patent No.: US 10,001,440 B2
(45) Date of Patent: Jun. 19, 2018

(54) OBSERVATION APPARATUS AND OBSERVATION METHOD

(71) Applicant: OLYMPUS CORPORATION, Shibuya-ku, Tokyo (JP)

(72) Inventor: Susumu Honda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 866 days.

(21) Appl. No.: 14/201,418

(22) Filed: Mar. 7, 2014

(65) Prior Publication Data

US 2014/0186856 A1 Jul. 3, 2014

Related U.S. Application Data

(62) Division of application No. 13/152,539, filed on Jun. 3, 2011, now abandoned.

(30) Foreign Application Priority Data

Jun. 9, 2010 (JP) ................... 2010-131998

(51) Int. Cl.
| | |
|---|---|
| G01N 21/64 | (2006.01) |
| G02B 21/36 | (2006.01) |
| G01N 15/14 | (2006.01) |
| G02B 21/16 | (2006.01) |

(52) U.S. Cl.
CPC ..... *G01N 21/6458* (2013.01); *G01N 21/6428* (2013.01); *G02B 21/16* (2013.01); *G02B 21/367* (2013.01); *G01N 2015/1472* (2013.01); *G01N 2021/6419* (2013.01); *G01N 2021/6421* (2013.01); *G01N 2021/6441* (2013.01)

(58) Field of Classification Search
None
See application file for complete search history.

(56) References Cited

U.S. PATENT DOCUMENTS

| | | | | |
|---|---|---|---|---|
| 6,459,484 B1 * | 10/2002 | Yokoi | ....................... | G01J 3/02 356/318 |
| 2002/0009719 A1 | 1/2002 | Walt et al. | | |
| 2007/0081233 A1 | 4/2007 | Hattori | | |
| 2007/0120069 A1 | 5/2007 | Takamizawa | | |
| 2008/0185533 A1 | 8/2008 | Kimura et al. | | |
| 2008/0290293 A1 | 11/2008 | Motomura | | |
| 2009/0166570 A1 * | 7/2009 | Honda | ................. | G01N 21/645 250/582 |
| 2009/0181396 A1 | 7/2009 | Luong et al. | | |
| 2010/0039701 A1 | 2/2010 | Tsurumune | | |
| 2010/0225910 A1 | 9/2010 | Wagner-Conrad et al. | | |

FOREIGN PATENT DOCUMENTS

| | | |
|---|---|---|
| EP | 1 793 257 A1 | 6/2007 |
| EP | 1 953 579 A1 | 8/2008 |
| JP | 10-206742 A | 8/1998 |
| JP | 2004-110017 A | 4/2004 |
| JP | 2006-003521 A | 1/2006 |
| JP | 2006-220818 A | 8/2006 |
| JP | 2008-009395 A | 1/2008 |
| JP | 2008-281720 A | 11/2008 |
| JP | 2009-145550 A | 7/2009 |
| WO | WO 2009/056205 A1 | 5/2009 |

OTHER PUBLICATIONS

Extended European Search Report (EESR) dated Aug. 5, 2011 (in English) in counterpart European Application No. 11004615.8.

* cited by examiner

*Primary Examiner* — Ram R Shukla
*Assistant Examiner* — Ellen J Marcsisin
(74) *Attorney, Agent, or Firm* — Holtz, Holtz & Volek PC

(57) ABSTRACT

An observation apparatus and an observation method are provided. The observation apparatus includes a light source that emits illumination light used to observe a specimen to which a fluorescent substance that specifically binds to or is expressed in a stimulus target has been supplied, an illumination optical system that radiates the illumination light emitted from the light source 11 onto the specimen, a deflecting device that changes an area of the specimen to be irradiated with the illumination light, a wavelength selecting section that selects the wavelength of illumination light to be radiated onto the specimen, an observation optical system that collects light from the specimen, a detector that detects the light collected by the observation optical system, an image processing section that generates an image from the light detected by the detector, and a control section that controls these components.

8 Claims, 13 Drawing Sheets

| | STIMULATION POSITION | STIMULATION | OBSERVATION |
|---|---|---|---|
| | Dye1 | Dye2 | Dye3 |
| WAVELENGTH | λ1 | λ2 | λ3 |
| AREA | P1 | P2 | P1 |

IMAGE PROCESSING AREA IS CHANGED

STEP 0: IRRADIATE AREA P1 WITH λ3 (OBSERVATION)
STEP 1: IRRADIATE AREA P1 WITH λ1 (OBSERVATION)
STEP 2: EXTRACT RADIANCE AREAS P2 FROM IMAGE OF P1
STEP 3: IRRADIATE AREAS P2 WITH λ2 (STIMULATION)
STEP 6: IRRADIATE AREA P1 WITH λ3 (OBSERVATION)

OBSERVATION APPARATUS AND OBSERVATION METHOD

This is a Divisional of U.S. application Ser. No. 13/152,539, filed Jun. 3, 2011, which is based upon and claims the benefit of priority from Japanese Patent Application No. 2010-131998, filed Jun. 9, 2010, the entire contents of both of which are incorporated herein by reference.

BACKGROUND OF THE INVENTION

1. Field of the Invention

The present invention relates to an observation apparatus and an observation method, used to observe living tissue, such as a cell, for example.

2. Description of Related Art

There are known observation apparatuses in the related art that are used to observe how the position and the shape of a cell change over time (for example, see Japanese Unexamined Patent Application, Publication No. 2008-281720, Japanese Unexamined Patent Application, Publication No. Hei-10-206742, and Japanese Unexamined Patent Application, Publication No. 2006-220818).

BRIEF SUMMARY OF THE INVENTION

An object of the present invention is to provide an observation apparatus and an observation method, capable of changing the stimulation position in accordance with the position and the shape of a cell and of observing the cell immediately after stimulation.

In order to achieve the above-described object, the present invention employs the following solutions.

According to a first aspect, the present invention provides an observation apparatus including: at least one light source that emits illumination light used to observe a specimen to which a fluorescent substance that specifically binds to or is expressed in a stimulus target has been supplied; an illumination optical system that radiates the illumination light emitted from the light source onto the specimen; a deflecting section that changes an area of the specimen to be irradiated with the illumination light; a wavelength selecting section that selects the wavelength of the illumination light to be radiated onto the specimen; an observation optical system that collects light from the specimen; at least one light detector that detects the light collected by the observation optical system; an image generation section that generates an image from the light detected by the light detector; and a control section that controls these components, in which the control section performs: fluorescent-substance extraction processing in which light having a first wavelength used to excite the fluorescent substance that specifically binds to or is expressed in the stimulus target included in the specimen is selected by the wavelength selecting section, and the fluorescent substance is extracted from a fluorescence image generated by the image generation section based on fluorescence produced from the fluorescent substance when the light having the first wavelength is radiated; stimulation processing in which light having a second wavelength used to stimulate the stimulus target is selected by the wavelength selecting section, and the illumination optical system radiates the light having the second wavelength onto the position of the fluorescent substance extracted in the fluorescent-substance extraction processing, through the deflecting section; and image generation processing in which light having a third wavelength used to acquire an image of the specimen is selected by the wavelength selecting section, and an image of the specimen that includes the stimulus target is generated by the image generation section.

According to the above-described aspect, the wavelength of illumination light to be radiated onto the specimen is selected by the wavelength selecting section, and light having the selected wavelength is radiated onto the specimen by the illumination optical system. Light thus produced from the specimen is collected by the observation optical system and is detected by the light detector, and an image is generated from the detected light by the image generation section. At this time, the image generation section may acquire a scan image by using the deflecting section and the light detector or may acquire an image by using, for example, a camera (CCD) provided for the light detector, instead of using the deflecting section.

In this case, the control section controls the above-described respective components to perform the fluorescent-substance extraction processing, the stimulation processing, and the image generation processing.

In the fluorescent-substance extraction processing, light having the first wavelength, used to excite the fluorescent substance that specifically binds to or is expressed in the stimulus target included in the specimen, is selected by the wavelength selecting section, and the fluorescent substance is extracted from a fluorescence image generated by the image generation section. Specifically, in the fluorescent-substance extraction processing, when the light having the first wavelength is radiated onto the specimen, the fluorescent substance included in the specimen is excited, producing fluorescence, and a fluorescence image of the fluorescent substance that specifically binds to or is expressed in the stimulus target is generated by detecting the fluorescence. Then, an area of the stimulus target is extracted from the thus-generated fluorescence image.

In the stimulation processing, light having the second wavelength, used to stimulate the stimulus target, is selected by the wavelength selecting section, and the illumination optical system radiates the light having the second wavelength onto the area of the stimulus target extracted in the fluorescent-substance extraction processing, through the deflecting section. Specifically, in the stimulation processing, the position of the stimulus target is identified based on the fluorescence image generated in the fluorescent-substance extraction processing, and the light having the second wavelength is radiated onto the position of the stimulus target by operating the deflecting section. Thus, the stimulus target is stimulated.

In the image generation processing, the light having the third wavelength, used to acquire an image of the specimen, is selected by the wavelength selecting section, and an image of the specimen that includes the stimulus target is generated by the image generation section. Specifically, in the image generation processing, an image of the specimen in which the stimulus target has been stimulated in the stimulation processing is acquired.

As described above, by controlling the respective components, it is possible to detect the position of the stimulus target by using the light having the first wavelength, to stimulate the stimulus target by using the light having the second wavelength, and to acquire an image of the specimen immediately after the stimulation by using the light having the third wavelength. Thus, it is possible to change the stimulation position in accordance with the position and the shape of the stimulus target included in the specimen, to observe the specimen immediately after the stimulation, and to improve the accuracy of observation of the specimen.

Note that, in the above-described processing, excitation is performed to produce fluorescence used to observe the substance, and stimulation is performed to cause a photochemical alteration in the substance to activate the substance, thereby giving an influence (effect) to the periphery of the substance.

Although the deflecting section is essential for the light having the second wavelength, it may be provided or omitted for the light having the first wavelength and the light having the third wavelength, and, for example, observation with an ordinary microscope can be used instead.

In the above-described aspect, a first light source that emits light having the first wavelength and light having the third wavelength and a second light source that emits light having the second wavelength may be included, in which the light detector may detect fluorescence produced from the specimen when the light having the first wavelength and the light having the third wavelength are radiated.

By doing so, it is possible to simultaneously emit the light having the second wavelength, used to stimulate the stimulus target, from the second light source and the light having the third wavelength, used to acquire an image of the specimen, from the first light source. Thus, it is possible to observe, in real time, the specimen when a stimulus is given and to improve the accuracy of observation of the specimen.

In the above-described aspect, a first light source that emits light having the third wavelength, a second light source that emits light having the first wavelength and light having the second wavelength, a first light detector that detects fluorescence produced from the specimen when the light having the third wavelength is radiated, and a second light detector that detects fluorescence produced from the specimen when the light having the first wavelength is radiated may be included, in which the control section may extract the stimulus target from an image generated by the image generation section based on the fluorescence detected by the second light detector.

By doing so, it is possible to generate an image used to identify the position of the stimulus target from the light detected by the second light detector and to generate an image of the specimen in which the stimulus target has been stimulated from the light detected by the first light detector; thus, the specimen can be continuously observed at the same time as image processing is being performed. Furthermore, it is possible to simultaneously emit the light having the second wavelength, used to stimulate the stimulus target, from the second light source and the light having the third wavelength, used to acquire an image of the specimen, from the first light source. Thus, it is possible to observe the specimen when a stimulus is given and to improve the accuracy of observation of the specimen.

In the above-described aspect, a first light source that emits light having the third wavelength, a second light source that emits light having the second wavelength, a third light source that emits light having the first wavelength, a first light detector that detects fluorescence produced from the specimen when the light having the third wavelength is radiated, and a second light detector that detects fluorescence produced from the specimen when the light having the first wavelength is radiated may be included, in which the control section may extract the fluorescent substance from a fluorescence image generated by the image generation section based on the fluorescence detected by the second light detector.

By doing so, it is possible to generate a fluorescence image used to identify the position of the stimulus target from the light detected by the second light detector and to generate an image of the specimen in which the stimulus target has been stimulated from the light detected by the first light detector; thus, the specimen can be continuously observed at the same time as image processing is being performed. Furthermore, it is possible to simultaneously emit the light having the first wavelength, used to identify the position of the stimulus target, from the third light source, the light having the second wavelength, used to stimulate the stimulus target, from the second light source, and the light having the third wavelength, used to acquire an image of the specimen, from the first light source. Thus, even if the specimen is considerably changed in position and shape, it is possible to observe the specimen when a stimulus is given and to improve the accuracy of observation of the specimen.

In the above-described aspect, the observation optical system may have a galvanometer mirror.

By doing so, it is possible to scan the specimen with illumination light from the light source by operating the galvanometer mirror and to generate an image of the specimen by associating the scanning position with the intensity of the light from the specimen that has been detected by the light detector. Thus, the light detector can be reduced in size.

In the above-described aspect, the deflecting section may be a galvanometer mirror.

An area of the specimen to be irradiated with the illumination light radiated by the illumination optical system can be changed by operating the galvanometer mirror.

In the above-described aspect, the deflecting section may be a microdevice array on which a plurality of microdevices that reflect or transmit light radiated from the illumination optical system are arrayed.

By doing so, an area of the specimen to be irradiated with the illumination light radiated by the illumination optical system can be changed by switching the microdevices, which reflect or transmit the light radiated from the illumination optical system.

In the above-described aspect, a recording section that records the image generated by the image generation section may be included, in which the control section may record in the recording section a fluorescence image of the specimen generated by the image generation section when the light having the first wavelength is radiated.

By doing so, the fluorescence image of the specimen generated when the light having the first wavelength, used to identify the position of the stimulus target, is radiated can be recorded in the recording section. Thus, it is possible to observe temporal changes in the position and the shape of the stimulus target.

According to a second aspect, the present invention provides an observation method including: a fluorescent-substance extraction step of supplying a fluorescent substance that specifically binds to or is expressed in a stimulus target to a specimen to label the stimulus target with the fluorescent substance and of extracting the fluorescent substance by processing a fluorescence image that is acquired by irradiating the specimen with light having a first wavelength used to excite the fluorescent substance; a stimulation step of radiating light having a second wavelength used to stimulate the stimulus target, onto the position of the fluorescent substance extracted in the fluorescent-substance extraction step; and an image generation step of radiating light having a third wavelength used to acquire an image of the specimen, onto the specimen to generate an image of the specimen that includes the stimulus target stimulated in the stimulation step.

According to the above-described aspect, the specimen is observed in the fluorescent-substance extraction step, the stimulation step, and the image generation step, in this order.

In the fluorescent-substance extraction step, when the light having the first wavelength is radiated onto the specimen, the fluorescent substance that specifically binds to or is expressed in the stimulus target included in the specimen is excited, producing fluorescence from the fluorescent substance, and a fluorescence image of the fluorescent substance is generated by detecting the fluorescence. Then, the position of the stimulus target is identified by extracting the position where the fluorescent substance exists based on the thus-generated fluorescence image.

In the stimulation step, the light having the second wavelength is radiated onto the position of the stimulus target identified in the fluorescent-substance extraction step. Thus, the stimulus target is stimulated.

In the image generation step, an image of the specimen in which the stimulus target has been stimulated in the stimulation step is acquired.

As described above, when the specimen is observed in the above-described order of steps, it is possible to change the stimulation position in accordance with the position and the shape of the stimulus target included in the specimen, to observe the specimen immediately after stimulation, and to improve the accuracy of observation of the specimen.

According to the present invention, an advantage is afforded in that it is possible to change the stimulation position in accordance with the position and the shape of a cell and to observe the cell immediately after stimulation.

DETAILED DESCRIPTION OF THE INVENTION

First Embodiment

A microscope 1 according to a first embodiment of the present invention will be described below with reference to the drawings.

Figure 1:
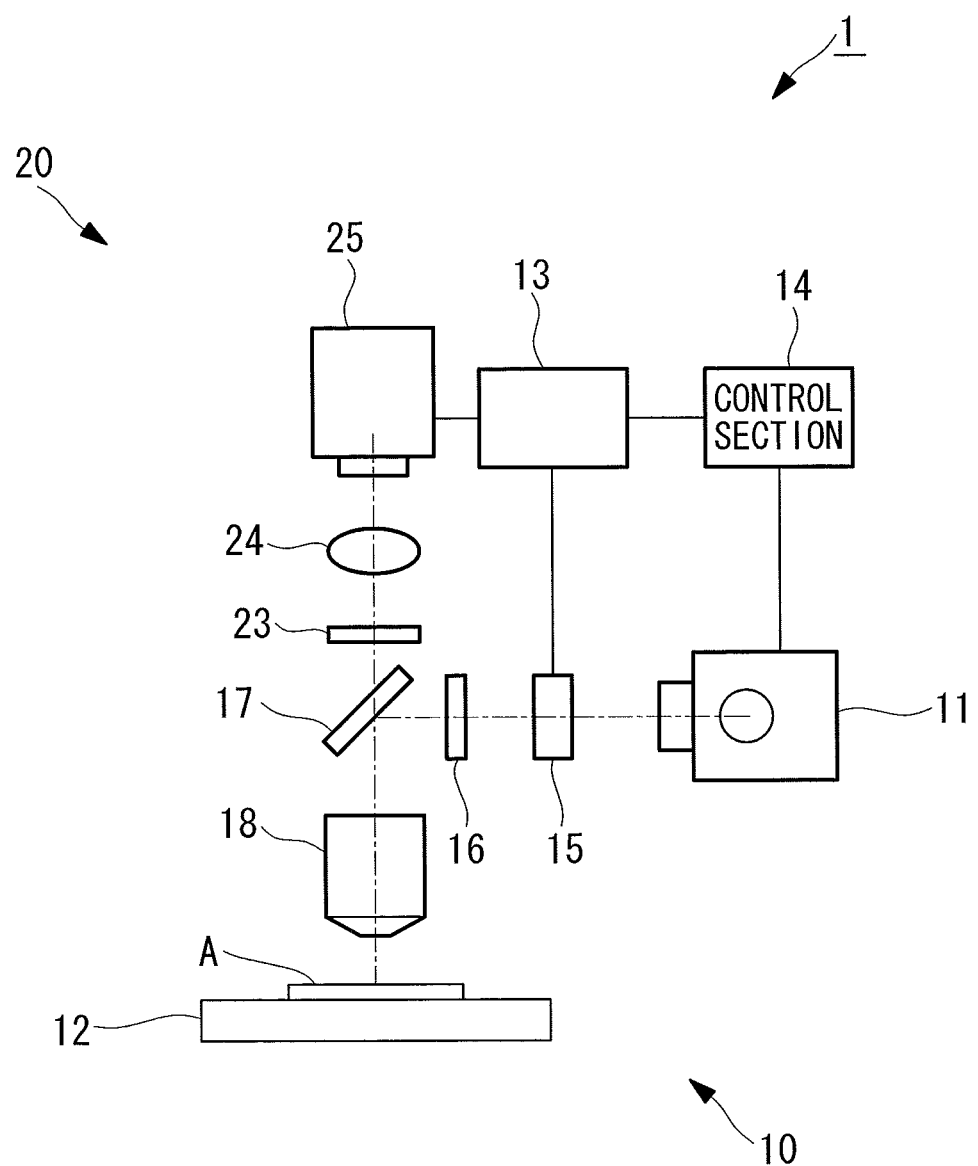
FIG. 1 is a diagram showing, in outline, the configuration of a microscope according to a first embodiment of the present invention.

As shown in FIG. 1, the microscope 1 of this embodiment includes a light source 11 that emits illumination light, a stage 12 on which a specimen A is placed, an illumination optical system 10 that irradiates the specimen A with the illumination light emitted from the light source 11, an observation optical system 20 that collects light from the specimen A, an image processing section (image generation section) 13 that generates an image from light coming from the specimen A, collected by the observation optical system 20, and a control section 14 that controls the above-described components.

The microscope 1 is used to observe a cranial nerve system, for example, and to stimulate ChR (channelrhodopsin) to observe a calcium reaction immediately after stimulation.

The light source 11 emits illumination light used to observe the specimen A to which a fluorescent substance that specifically binds to or is expressed in a stimulus target has been supplied.

Specifically, based on an instruction from the control section 14, to be described later, the light source 11 selectively emits light having a wavelength $\lambda 1$ used to excite the fluorescent substance that specifically binds to or is expressed in the stimulus target (channelrhodopsin) included in the specimen A, light having a wavelength $\lambda 2$ used to stimulate the stimulus target (channelrhodopsin), and light having a wavelength $\lambda 3$ used to detect an observation object (calcium) (specifically, used to acquire an image of the specimen A).

Note that, in the above-described processing, excitation is performed to produce fluorescence used to observe the substance, and stimulation is performed to cause a photochemical alteration in the substance to activate the substance, thereby giving an influence (effect) to the periphery of the substance.

The illumination optical system 10 includes a deflecting device (deflecting section) 15 that deflects illumination light emitted from the light source 11, an Ex filter (excitation filter) 16 that transmits light having a predetermined wavelength range, an objective lens 18 that is disposed facing the specimen A, and a dichroic mirror 17 that is disposed at the intersection of the optical axis of the light source 11 with the optical axis of the objective lens 18.

The deflecting device 15 is, for example, a DMD (digital mirror device) on which a plurality of movable micromirrors (microdevices) are arrayed. With this structure, by operating the movable micromirrors (turning them ON/OFF), the deflecting device 15 selectively reflects part or all of the illumination light emitted from the light source 11 toward the dichroic mirror 17 to change an area of the specimen A irradiated with the illumination light.

The objective lens 18 irradiates the specimen A with the illumination light that has been transmitted through the Ex filter 16 and also collects light from the specimen A. Here, light from the specimen A includes light returning from the specimen A and fluorescence produced in the specimen A, for example.

The dichroic mirror 17 reflects the illumination light from the light source 11 that has been transmitted through the Ex filter 16 toward the objective lens 18 and also transmits the light from the specimen A that has been collected by the objective lens 18. Thus, the dichroic mirror 17 separates the illumination light from the light source 11 and the light from the specimen A.

The observation optical system 20 includes an Em filter (fluorescence filter) 23 that transmits light having a predetermined wavelength range, an imaging lens 24 that forms, on a detector 25, an image of the light from the specimen A that has been transmitted through the Em filter 23, and the detector (light detector) 25 that detects the light from the specimen A whose image has been formed by the imaging lens 24.

Of the light from the specimen A that has been transmitted through the dichroic mirror 17, the Em filter 23 transmits the fluorescence produced in the specimen A and blocks the illumination light from the light source 11.

The detector 25 is, for example, a CCD (charge coupled device) and outputs to the image processing section 13 an electrical signal that is obtained by photoelectrically converting the detected light.

The image processing section 13 generates an image of the specimen A based on the area of the specimen A irradiated with the illumination light, which is changed by the deflecting device 15, and the intensity of the light detected by the detector 25.

The control section 14 controls the light source 11 to select the wavelength of illumination light to be radiated onto the specimen A. The control section 14 also controls the respective components, which include the light source 11, to perform fluorescent-substance extraction processing for extracting the stimulus target included in the specimen A, stimulation processing for stimulating the stimulus target included in the specimen A, and image generation processing for generating an image of the specimen A that includes the stimulus target. Specific processes to be performed by the control section 14 during the above-described processing will be described below.

In the fluorescent-substance extraction processing, the control section 14 selects, as illumination light to be radiated from the light source 11, light having the wavelength $\lambda 1$, used to excite the fluorescent substance that specifically binds to or is expressed in the stimulus target (channelrhodopsin) included in the specimen A, to extract the fluorescent substance (the positions of the stimulus target) from a fluorescence image generated by the image processing section 13 based on fluorescence produced from the fluorescent substance when irradiated with the light having the wavelength $\lambda 1$.

In the stimulation processing, the control section 14 selects, as illumination light to be radiated from the light source 11, light having the wavelength $\lambda 2$, used to stimulate the stimulus target (channelrhodopsin), to make the illumination optical system 10 radiate the light having the wavelength $\lambda 2$ onto the positions of the fluorescent substance extracted in the fluorescent-substance extraction processing.

In the image generation processing, the control section 14 selects, as illumination light to be radiated from the light source 11, light having the wavelength $\lambda 3$, used to detect the observation object (calcium) (specifically, used to acquire an image of the specimen A), to make the image processing section 13 generate an image of the specimen A that includes the stimulus target.

Figure 2:
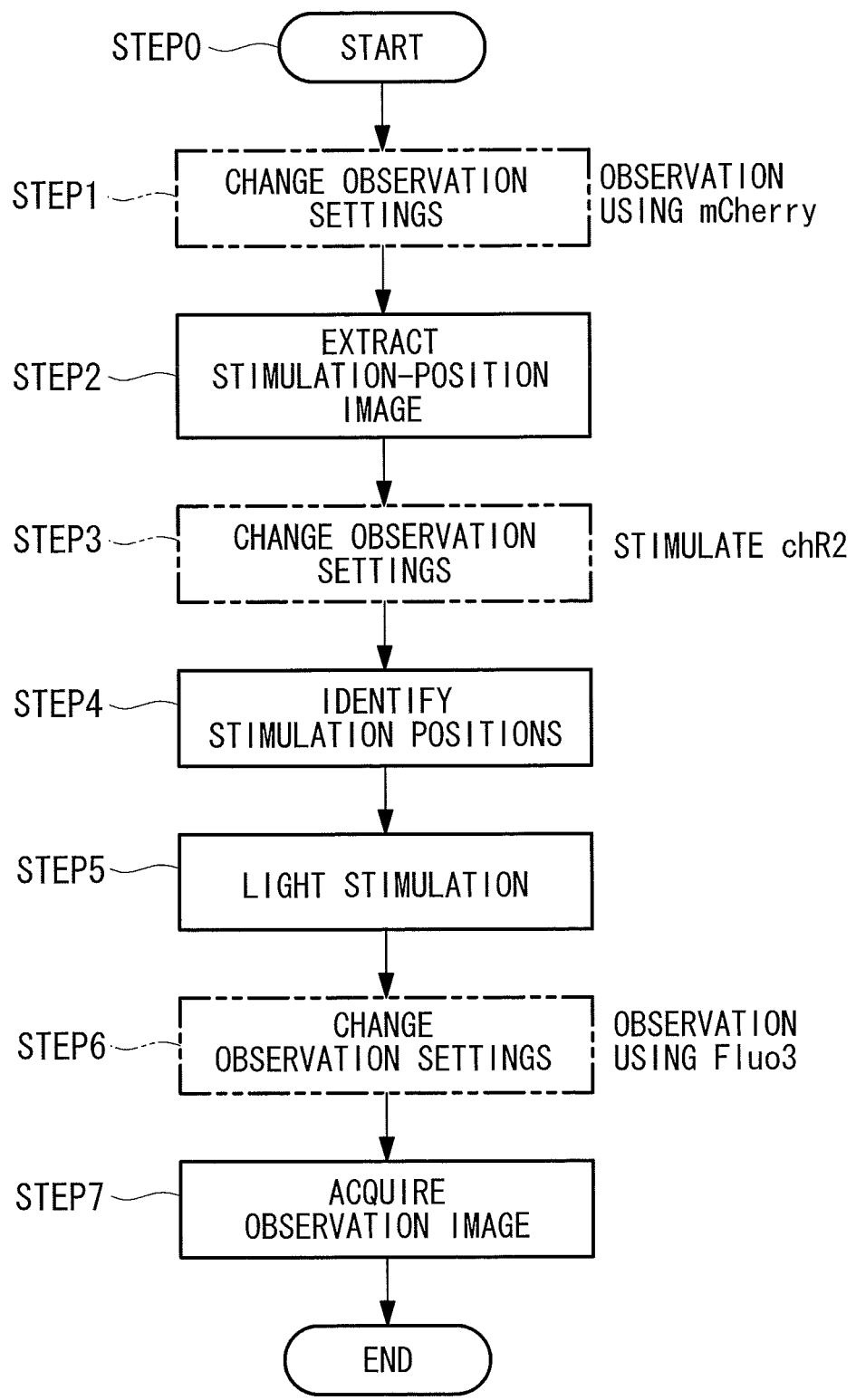
FIG. 2 is a flowchart showing processing performed by the microscope shown in FIG. 1.

The operation of the microscope 1, having the above-described configuration, will be described below based on a flowchart shown in FIG. 2.

A description will be given of a specific example case where, in observing the cranial nerve system, the stimulus target (ChR2) is stimulated while viewing the observation object (calcium) by using Fluo3 (fluorescence produced in the specimen A). The stimulus target (ChR2) is labeled with mCherry (fluorescent substance that specifically binds to or is expressed in channelrhodopsin ChR2, which is the stimulus target).

According to the microscope 1, having the above-described configuration, the wavelength of illumination light to be radiated from the light source 11 is selected by the control section 14, and illumination light having the selected wavelength is radiated onto the specimen A by the illumination optical system 10. At this time, the area of the specimen A irradiated with the illumination light is changed by the deflecting device 15. Light produced in the specimen A is collected by the observation optical system 20 and is detected by the detector 25, and an image is generated from the detected light by the image processing section 13.

In this case, the control section 14 controls the respective components to perform the fluorescent-substance extraction processing, the stimulation processing, and the image generation processing.

Figure 3:
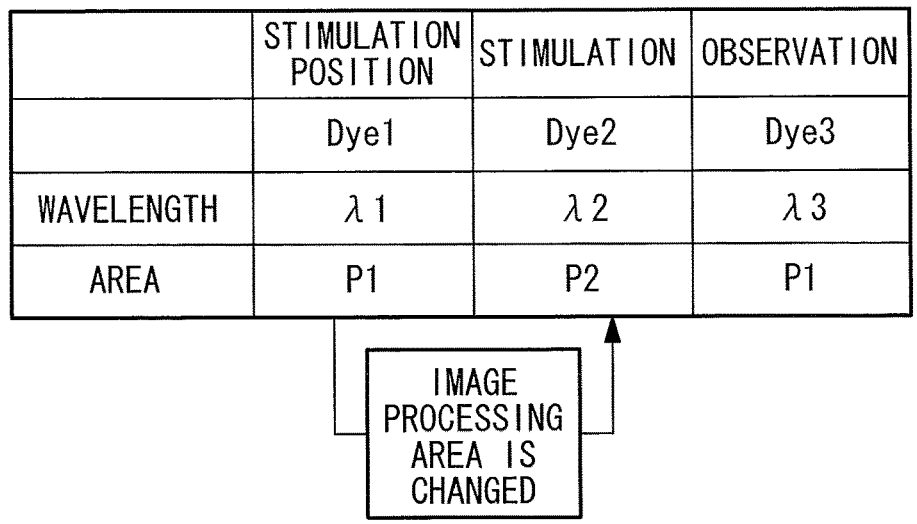
FIG. 3 is a diagram for explaining the wavelengths of illumination light and irradiated areas selected in the processing shown in FIG. 2.
Figure 4A:
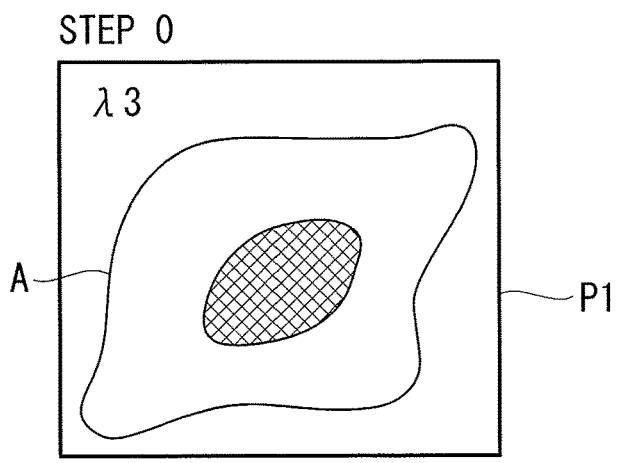
FIG. 4A is a diagram showing an example image acquired in STEP 0 shown in FIG. 2.

As shown in FIG. 3, in the initial state (STEP 0), light having the wavelength $\lambda 3$, used to acquire an image of the specimen A, is selected as illumination light to be radiated. As an area to be irradiated with the illumination light, an area P1 corresponding to the entire field of view is selected, for example. In this case, the light having the wavelength $\lambda 3$ is radiated onto the area P1, and an image of the specimen A that includes the stimulus target is generated by the image processing section 13. The image acquired in this case is shown in FIG. 4A.

Figure 4B:
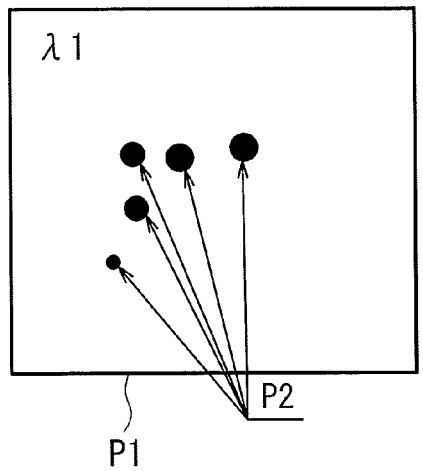
FIG. 4B is a diagram showing an example image acquired in STEPS 1 and 2 shown in FIG. 2.

Next, observation settings are changed (STEP 1), and the fluorescent-substance extraction processing is performed. In this case, as shown in FIG. 3, light having the wavelength $\lambda 1$, used to excite the fluorescent substance that specifically binds to or is expressed in the stimulus target included in the specimen A, is selected as illumination light to be radiated. The area P1 is selected as an area to be irradiated with the illumination light. Thus, the fluorescent substance (the positions of the stimulus target) is extracted from an image generated by the image processing section 13 (STEP 2). Specifically, in the fluorescent-substance extraction processing, when light having the wavelength λ1 is radiated onto the area P1, the fluorescent substance included in the area P1 is excited, producing fluorescence from the fluorescent substance, and a fluorescence image of the fluorescent substance is generated by detecting the fluorescence. The image (including black circles) acquired in this case is shown in FIG. 4B. Then, as the areas of the stimulus target, areas P2 are extracted from the thus-generated fluorescence image of the fluorescent substance.

Figure 4C:
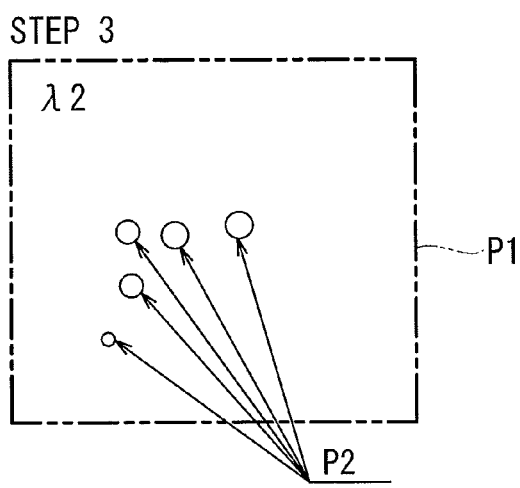
FIG. 4C is a diagram showing an example image acquired in STEP 3 shown in FIG. 2.

Next, the observation settings are changed (STEP 3), and the stimulation processing is performed. In this case, as shown in FIG. 3, light having the wavelength λ2, used to stimulate the stimulus target, is selected. As areas to be irradiated with the light having the wavelength λ2, the areas P2 of the fluorescent substance (the areas of the stimulus target) extracted in the fluorescent-substance extraction processing are selected. As a result, the light having the wavelength λ2 is radiated by the illumination optical system 10 onto the positions of the stimulus target extracted in the fluorescent-substance extraction processing. Specifically, in the stimulation processing, the positions of the stimulus target are identified based on the fluorescence image of the fluorescent substance generated in the fluorescent-substance extraction processing (STEP 4), and the light having the wavelength λ2 is radiated onto the stimulus target to stimulate the stimulus target (STEP 5). The image acquired in this case is shown in FIG. 4C.

Figure 4D:
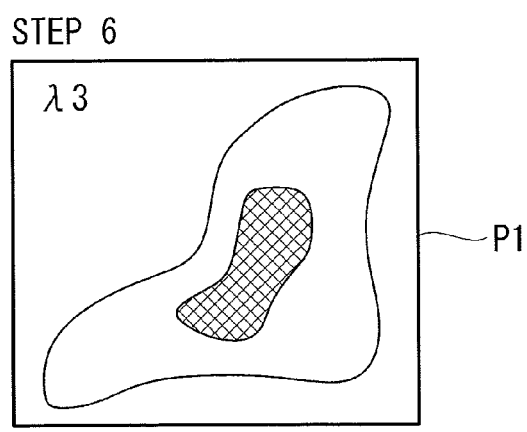
FIG. 4D is a diagram showing an example image acquired in STEP 6 shown in FIG. 2.

Next, the observation settings are changed (STEP 6), and the image generation processing is performed. In this case, as shown in FIG. 3, light having the wavelength λ3, used to acquire an image of the specimen A, is selected. The area P1 is selected as an area to be irradiated with the light having the wavelength λ3. As a result, an image of the specimen A that includes the stimulus target is generated by the image processing section 13. Specifically, in the image generation processing, an image of the specimen A in which the stimulus target has been stimulated in the stimulation processing is acquired (STEP 7). The image acquired in this case is shown in FIG. 4D.

As described above, according to the microscope 1 of this embodiment, by controlling the respective components, it is possible to detect the positions of the stimulus target by using light having the wavelength λ1, to stimulate the stimulus target by using light having the wavelength λ2, and to acquire an image of the specimen A in which the stimulus target has been stimulated, by using light having the wavelength λ3. Thus, it is possible to stimulate the specimen A in accordance with the positions and the shapes of the stimulus target included in the specimen A, to observe the specimen A immediately after the stimulation, and to improve the accuracy of observation of the specimen A.

Modification

Figure 5:
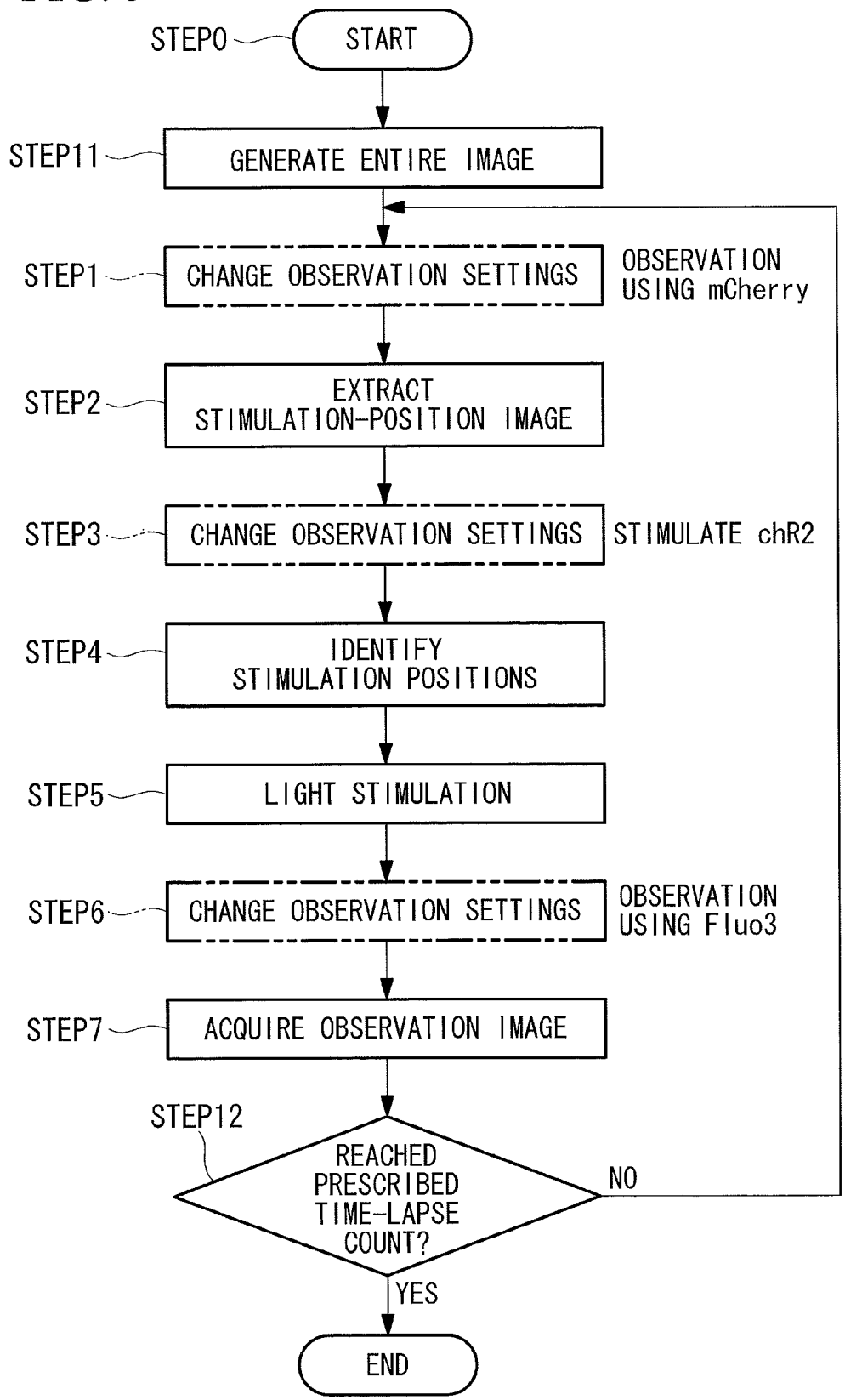
FIG. 5 is a flowchart showing processing performed by a microscope according to a modification of the microscope shown in FIG. 1.

A modification of the microscope 1 according to this embodiment will be described below mainly with reference to FIGS. 5 and 6.

In a microscope 1 of this modification, the control section 14 performs time-lapse observation of the specimen A and changes the positions and the shapes of the stimulus target included in the specimen A, based on an acquired image of the specimen A.

The fluorescent-substance extraction processing, the stimulation processing, and the image generation processing, which are performed by the control section 14, in the microscope 1 of this modification will be described below based on a flowchart shown in FIG. 5.

Figure 6A:
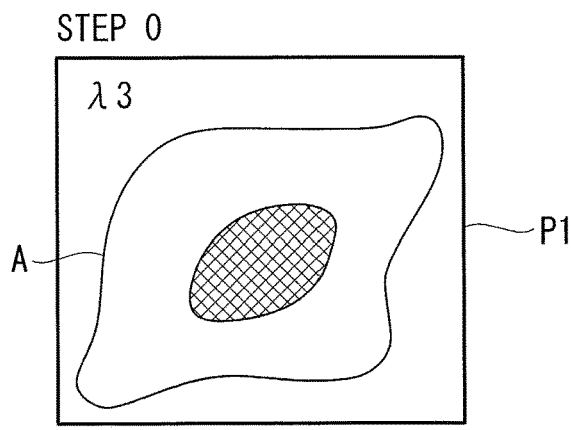
FIG. 6A is a diagram showing an example image acquired in STEP 0 shown in FIG. 5.

First, in the initial state (STEP 0), as shown in FIG. 3, light having the wavelength λ3, used to acquire an image of the specimen A, is selected as illumination light to be radiated. As an area to be irradiated with the illumination light, the area P1 corresponding to the entire field of view is selected, for example. In this case, the light having the wavelength λ3 is radiated onto the area P1, and an image of the entire specimen A that includes the stimulus target is generated by the image processing section 13 (STEP 11). The image acquired in this case is shown in FIG. 6A.

Figure 6B:
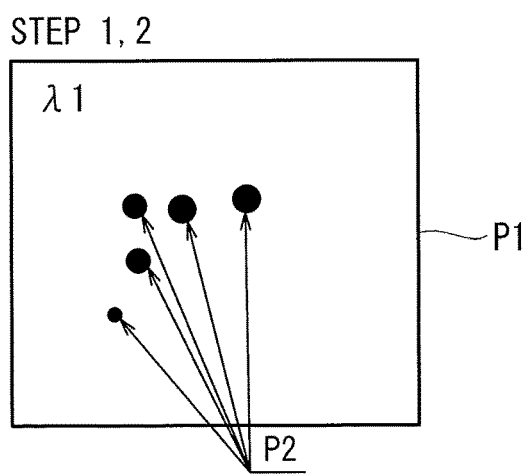
FIG. 6B is a diagram showing an example image acquired in STEPS 1 and 2 shown in FIG. 5.

Next, the observation settings are changed (STEP 1), and the fluorescent-substance extraction processing is performed. In this case, as shown in FIG. 3, light having the wavelength λ1, used to excite the fluorescent substance that specifically binds to or is expressed in the stimulus target included in the specimen A, is selected as illumination light to be radiated. The area P1 is selected as an area to be irradiated with the illumination light. Thus, the fluorescent substance (the positions of the stimulus target) is extracted from an image generated by the image processing section 13 (STEP 2). Specifically, in the fluorescent-substance extraction processing, when light having the wavelength λ1 is radiated onto the area P1, the fluorescent substance included in the area P1 is excited, producing fluorescence from the fluorescent substance, and a fluorescence image of the fluorescent substance is generated by detecting the fluorescence. The image (including black circles) acquired in this case is shown in FIG. 6B. Then, as the areas of the stimulus target, areas P2 are extracted from the thus-generated fluorescence image of the fluorescent substance.

Figure 6C:
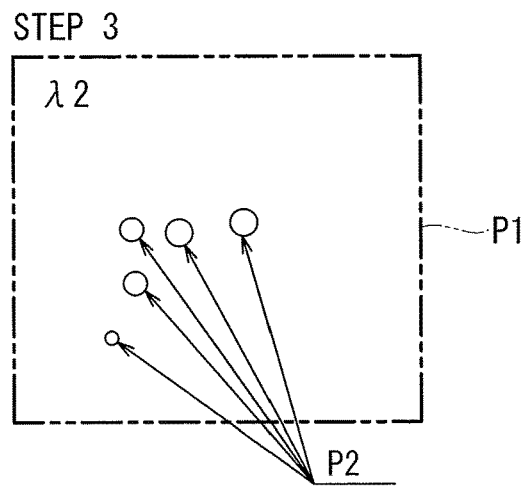
FIG. 6C is a diagram showing an example image acquired in STEP 3 shown in FIG. 5.

Next, the observation settings are changed (STEP 3), and the stimulation processing is performed. In this case, as shown in FIG. 3, light having the wavelength λ2, used to stimulate the stimulus target, is selected. As areas to be irradiated with the light having the wavelength λ2, the areas P2 of the fluorescent substance (the areas of the stimulus target) extracted in the fluorescent-substance extraction processing are selected. As a result, the light having the wavelength λ2 is radiated by the illumination optical system 10 onto the positions of the stimulus target extracted in the fluorescent-substance extraction processing. Specifically, in the stimulation processing, the positions of the stimulus target are identified based on the fluorescence image of the fluorescent substance generated in the fluorescent-substance extraction processing (STEP 4), and the light having the wavelength λ2 is radiated onto the stimulus target to stimulate the stimulus target (STEP 5). The image acquired in this case is shown in FIG. 6C.

Figure 6D:
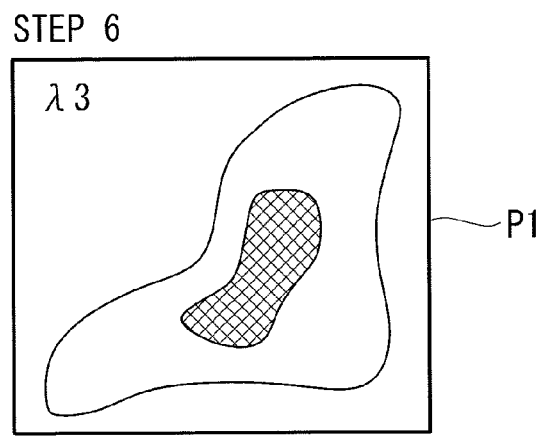
FIG. 6D is a diagram showing an example image acquired in STEP 6 shown in FIG. 5.

Next, the observation settings are changed (STEP 6), and the image generation processing is performed. In this case, as shown in FIG. 3, light having the wavelength λ3, used to acquire an image of the specimen A, is selected. The area P1 is selected as an area to be irradiated with the light having the wavelength λ3. As a result, an image of the specimen A that includes the stimulus target is generated by the image processing section 13. Specifically, in the image generation processing, an image of the specimen A in which the stimulus target has been stimulated in the stimulation processing is acquired (STEP 7). The image acquired in this case is shown in FIG. 6D.

Next, it is determined whether the number of acquired images of the specimen A reaches a prescribed time-lapse count, set in advance (STEP 12). In STEP 12, if the number of acquired images of the specimen A does not reach the prescribed time-lapse count, the flow returns to STEP 1, the observation settings are changed, and the fluorescent-substance extraction processing is performed again.

Figure 6E:
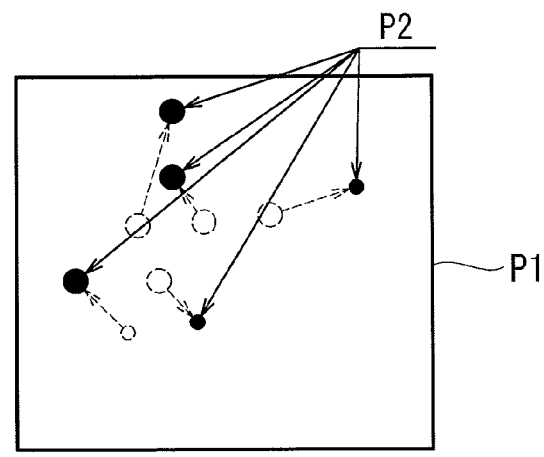
FIG. 6E is a diagram showing an example image acquired in STEPS 1 and 2 shown in FIG. 5, when stimulation positions are changed.

In this case, as described above, light having the wavelength λ1 is selected as illumination light to be radiated, and the area P1 is selected as an area to be irradiated with the illumination light. Thus, the fluorescent substance (the positions of the stimulus target) is extracted from an image generated by the image processing section 13 (STEP 2). The image (including black circles) acquired in this case is shown in FIG. 6E. In FIG. 6E, for example, since the state of the specimen A is changed, the positions and the shapes of the stimulus target included in the specimen A are changed. Note that, in FIG. 6E, dashed circles indicate the positions and the shapes of the stimulus target included in the specimen A before changing (specifically, the dashed circles correspond to the black circles shown in FIG. 6B). Then, as the areas of the stimulus target that has been changed in position and shape, the areas P2 are extracted from the thus-generated fluorescence image of the fluorescent substance.

Figure 6F:
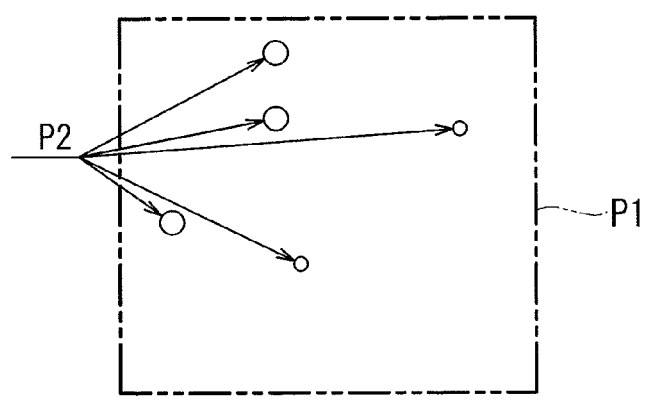
FIG. 6F is a diagram showing an example image acquired in STEP 3 shown in FIG. 5, when the stimulation positions are changed.

Next, the observation settings are changed (STEP 3), and the stimulation processing is performed. In this case, as described above, light having the wavelength λ2, used to stimulate the stimulus target, is selected, and the areas P2 of the stimulus target that has been changed in position and shape are selected as areas to be irradiated with the light having the wavelength λ2. As a result, the light having the wavelength λ2 is radiated by the illumination optical system 10 onto the positions of the stimulus target that has been changed in position and shape. The image acquired in this case is shown in FIG. 6F.

Thereafter, the above-described processing from STEP 4 to STEP 7 is repeated until the number of acquired images of the specimen A reaches the prescribed time-lapse count. Thus, the stimulus target that is changed in position and shape is stimulated, and the image of the specimen A in which the stimulus target has been stimulated is generated by the image processing section 13.

In STEP 12, the processing ends when the number of acquired images of the specimen A reaches the prescribed time-lapse count.

As described above, according to the microscope 1 of this modification, by controlling the respective components, it is possible to detect the positions of the stimulus target that is changed in position and shape, through time-lapse observation, to stimulate the stimulus target that has been changed in position and shape, and to acquire an image of the specimen A in which the stimulus target has been stimulated. Thus, it is possible to change the stimulation positions in accordance with the change in the positions and the shapes of the stimulus target included in the specimen A, to observe the specimen A immediately after the stimulation, and to improve the accuracy of observation of the specimen A.

Second Embodiment

A microscope 2 according to a second embodiment will be described below with reference to the drawings. The microscope 2 according to this embodiment and microscopes according to modifications will be described mainly in terms of the differences from the microscope 1 of the first embodiment, and a description of similarities will be omitted.

Figure 7:
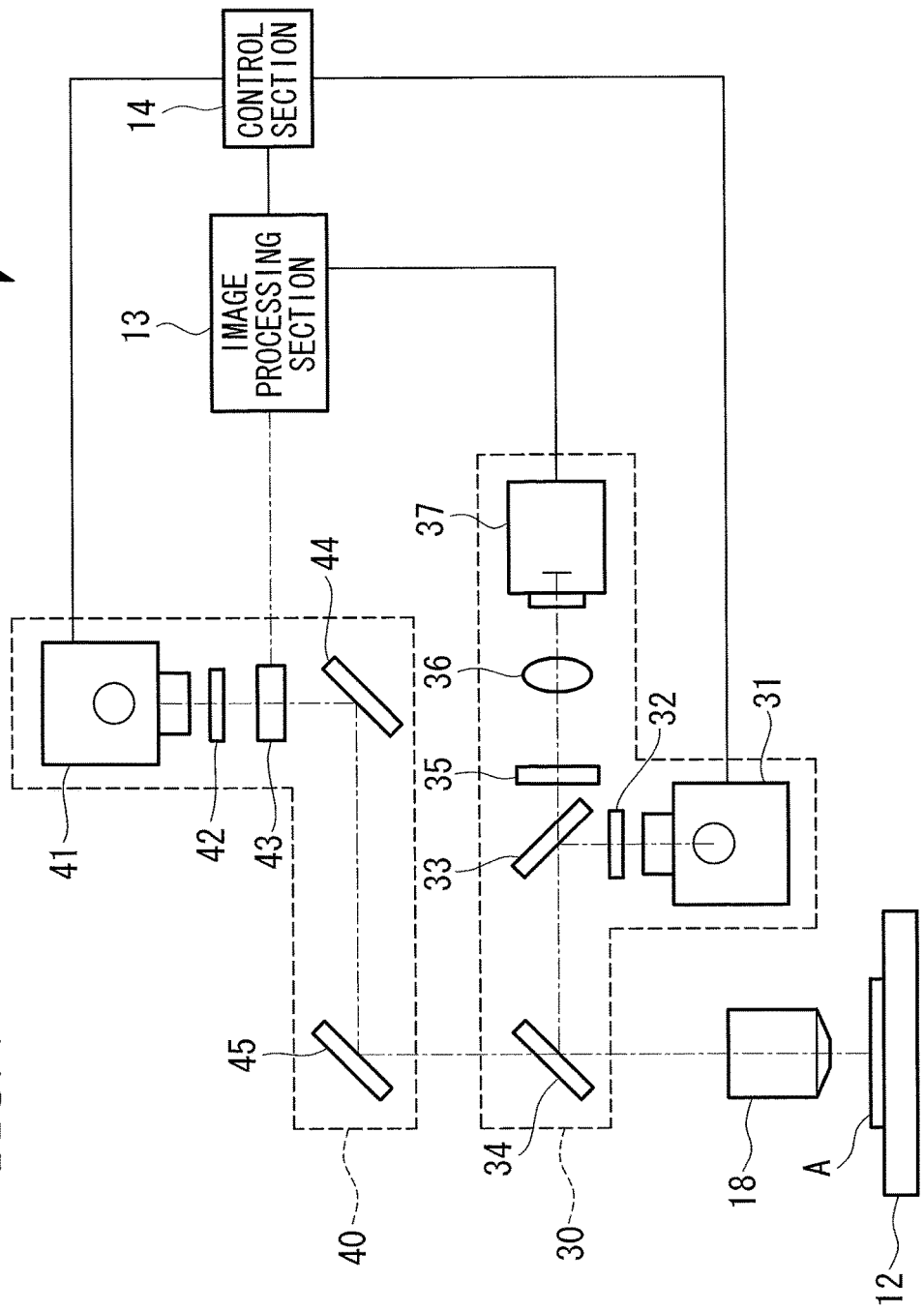
FIG. 7 is a diagram showing, in outline, the configuration of a microscope according to a second embodiment of the present invention.

As shown in FIG. 7, the microscope 2 of this embodiment includes a first optical system 30 that emits illumination light, a second optical system 40 that emits illumination light, the stage 12 on which the specimen A is placed, the objective lens 18 that is disposed facing the specimen A, and the image processing section (image generation section) 13 that generates an image from light coming from the specimen A, collected by the objective lens 18, and the control section 14 that controls these components.

The first optical system 30 is used to observe the specimen A and includes a first light source 31 that emits illumination light, an Ex filter (excitation filter) 32 that transmits light having a predetermined wavelength range, dichroic mirrors 33 and 34 that separate the illumination light and the light from the specimen A, an Em filter (fluorescence filter) 35 that transmits light having a predetermined wavelength range, an imaging lens 36 that forms, on a detector 37, an image of the light from the specimen A that has been transmitted through the Em filter 35, and the detector (light detector) 37 that detects the light from the specimen A whose image has been formed by the imaging lens 36.

The second optical system 40 is used to stimulate the stimulus target included in the specimen A and includes a second light source 41 that emits illumination light, an Ex filter (excitation filter) 42 that transmits light having a predetermined wavelength range, a deflecting device (deflecting section) 43 that deflects the illumination light emitted from the second light source 41, and mirrors 44 and 45 that reflect the illumination light deflected by the deflecting device 43.

The first light source 31 emits illumination light used to observe the specimen A to which a fluorescent substance that specifically binds to or is expressed in the stimulus target has been supplied.

Specifically, based on an instruction from the control section 14, the first light source 31 selectively emits light having the wavelength λ1, used to excite the fluorescent substance that specifically binds to or is expressed in the stimulus target (channelrhodopsin) included in the specimen A, and light having the wavelength λ3, used to detect the observation object (calcium) (specifically, used to acquire an image of the specimen A).

The second light source 41 emits illumination light used to stimulate the stimulus target.

Specifically, the second light source 41 emits light having the wavelength λ2, used to stimulate the stimulus target (channelrhodopsin), based on an instruction from the control section 14.

The control section 14 controls the first light source 31 and the second light source 41 to select the wavelength of illumination light to be radiated onto the specimen A. The control section 14 also controls the respective components, which include the first light source 31 and the second light source 41, to perform the fluorescent-substance extraction processing for extracting the fluorescent substance included in the specimen A, the stimulation processing for stimulating the stimulus target included in the specimen A, and the image generation processing for generating an image of the specimen A that includes the stimulus target. Specific processes to be performed by the control section 14 during the above-described processing will be described below.

In the fluorescent-substance extraction processing, the control section 14 operates the first light source 31. The control section 14 selects, as illumination light to be radiated from the first light source 31, light having the wavelength λ1, used to excite the fluorescent substance that specifically binds to or is expressed in the stimulus target (channelrhodopsin) included in the specimen A, to extract the fluorescent substance (the positions of the stimulus target) from a fluorescence image generated by the image processing section 13.

In the stimulation processing, the control section 14 operates the second light source 41. The control section 14 selects, as illumination light to be radiated onto the specimen A, light having the wavelength λ2, used to stimulate the stimulus target (channelrhodopsin), to cause the light having the wavelength λ2 to be radiated onto the positions of the stimulus target extracted in the fluorescent-substance extraction processing.

In the image generation processing, the control section 14 operates the first light source 31. The control section 14 selects, as illumination light to be radiated from the first light source 31, light having the wavelength λ3, used to acquire an image of the specimen A, to make the image processing section 13 generate an image of the specimen A that includes the stimulus target.

The operation of the microscope 2, having the above-described configuration, will be described below.

According to the microscope 2, having the above-described configuration, the control section 14 selects the wavelength of illumination light to be radiated onto the specimen A and causes light having the selected wavelength to be radiated onto the specimen A through the objective lens 18. At this time, the area of the specimen A irradiated with the illumination light is changed by the deflecting device 43. Light produced in the specimen A is collected by the objective lens 18 and is detected by the detector 37, and an image is generated from the detected light by the image processing section 13.

In this case, the control section 14 controls the first light source 31 and the second light source 41 to perform the fluorescent-substance extraction processing, the stimulation processing, and the image generation processing.

Specifically, the control section 14 controls the first light source 31 and the second light source 41 to switch illumination light to be radiated onto the specimen A and controls the respective components according to the switched illumination light, in the same manner as in the above-described first embodiment, to perform the fluorescent-substance extraction processing, the stimulation processing, and the image generation processing, as described below.

In the fluorescent-substance extraction processing, the first light source 31 is operated to radiate light having the wavelength λ1, used to excite the fluorescent substance that specifically binds to or is expressed in the stimulus target included in the specimen A, onto the specimen A to extract the fluorescent substance (the positions of the stimulus target) from an image generated by the image processing section 13.

In the stimulation processing, the second light source 41 is operated to radiate, as illumination light to be radiated onto the specimen A, light having the wavelength λ2, used to stimulate the stimulus target (channelrhodopsin), onto the positions of the stimulus target extracted in the fluorescent-substance extraction processing.

In the image generation processing, the first light source 31 is operated to radiate light having the wavelength λ3, used to acquire an image of the specimen A, onto the specimen A, and an image of the specimen A that includes the stimulus target is generated by the image processing section 13. Note that, since the different light sources are used, the stimulation processing and the image generation processing can be performed at the same time.

As described above, according to the microscope 2 of this embodiment, in addition to the same effects as those in the microscope 1 of the first embodiment, it is possible to simultaneously emit light having the wavelength λ2, used to stimulate the stimulus target, from the second light source 41 and light having the wavelength λ3, used to acquire an image of the specimen A, from the first light source 31. Thus, it is possible to observe, in real time, the specimen A when a stimulus is given and to improve the accuracy of observation of the specimen A.

First Modification

A first modification of the microscope 2 according to this embodiment will be described below with reference to FIG. 8.

In a microscope 3 of this modification, the first optical system 30 is used to observe the specimen A and has the same configuration as the microscope 2 of the above-described embodiment.

Figure 8:
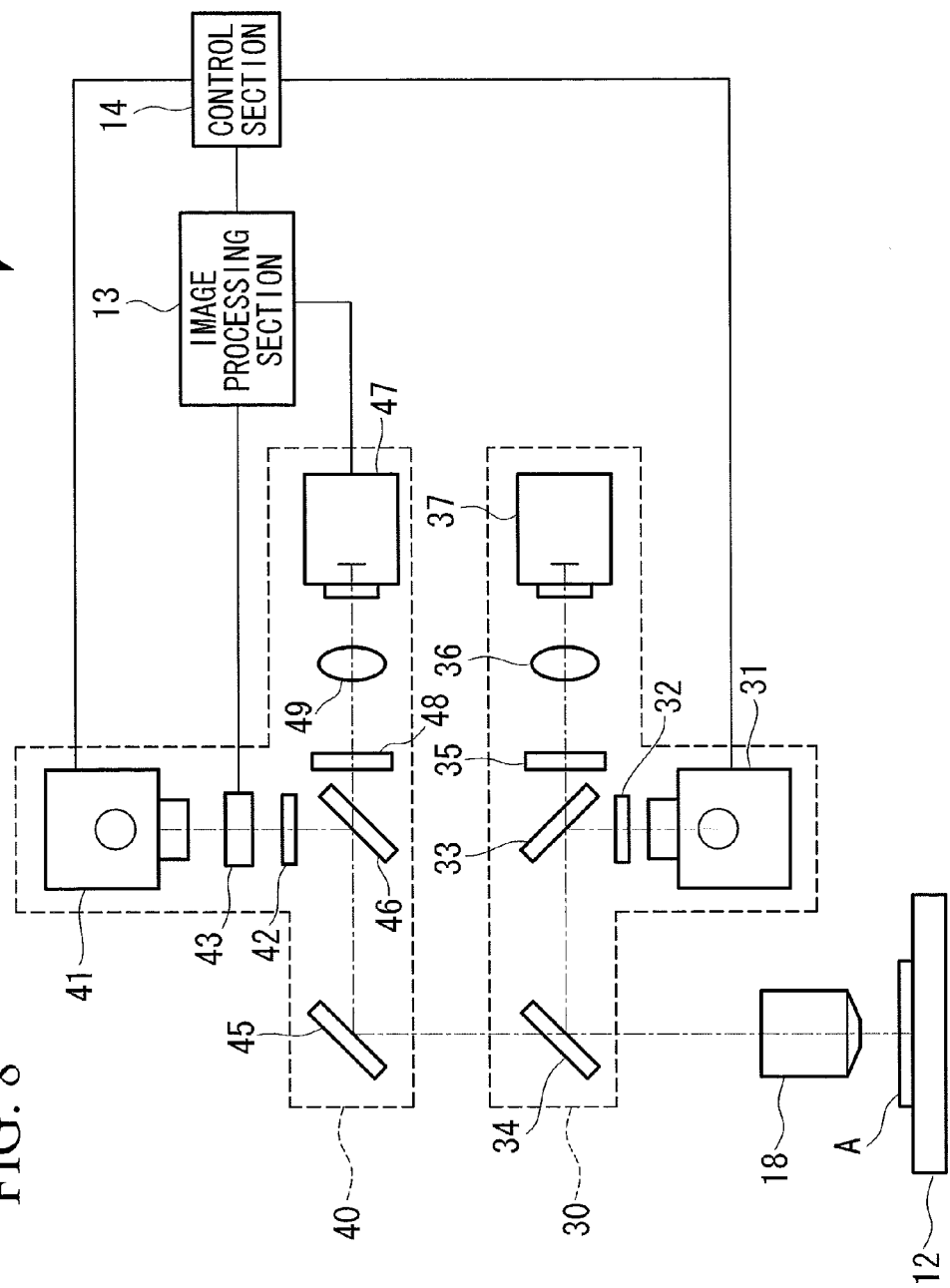
FIG. 8 is a diagram showing, in outline, the configuration of a microscope according to a first modification of the microscope shown in FIG. 7.

As shown in FIG. 8, the second optical system 40 is used to stimulate the stimulus target included in the specimen A and includes the second light source 41 that emits illumination light, the Ex filter (excitation filter) 42 that transmits light having a predetermined wavelength range, the deflecting device 43 that deflects the illumination light emitted from the second light source 41, the mirror 45 that reflects the illumination light deflected by the deflecting device 43, a dichroic mirror 46 that separates the illumination light and light from the specimen A, an Em filter (fluorescence filter) 48 that transmits light having a predetermined wavelength range, an imaging lens 49 that forms, on a second detector 47, an image of the light from the specimen A that has been transmitted through the Em filter 48, and the second detector (light detector) 47 that detects the light from the specimen A whose image has been formed by the imaging lens 49.

According to the microscope 3 of this modification, having the above-described configuration, it is possible to generate an image used to identify the positions of the stimulus target from the light detected by the second detector 47 and to generate an image of the specimen A in which the stimulus target has been stimulated from the light detected by the first detector 37; thus, the specimen A can be continuously observed at the same time as image processing being performed. Furthermore, it is possible to simultaneously emit light having the wavelength λ2, used to stimulate the stimulus target, from the second light source 41 and light having the wavelength λ3, used to acquire an image of the specimen A, from the first light source 31. Thus, it is possible to observe, in real time, the specimen A when a stimulus is given and to improve the accuracy of observation of the specimen A.

Second Modification

A second modification of the microscope 2 according to this embodiment will be described below with reference to FIG. 9.

In a microscope 4 of this modification, the first optical system 30 is used to observe the specimen A and has the same configuration as the microscope 2 of the above-described embodiment.

Figure 9:
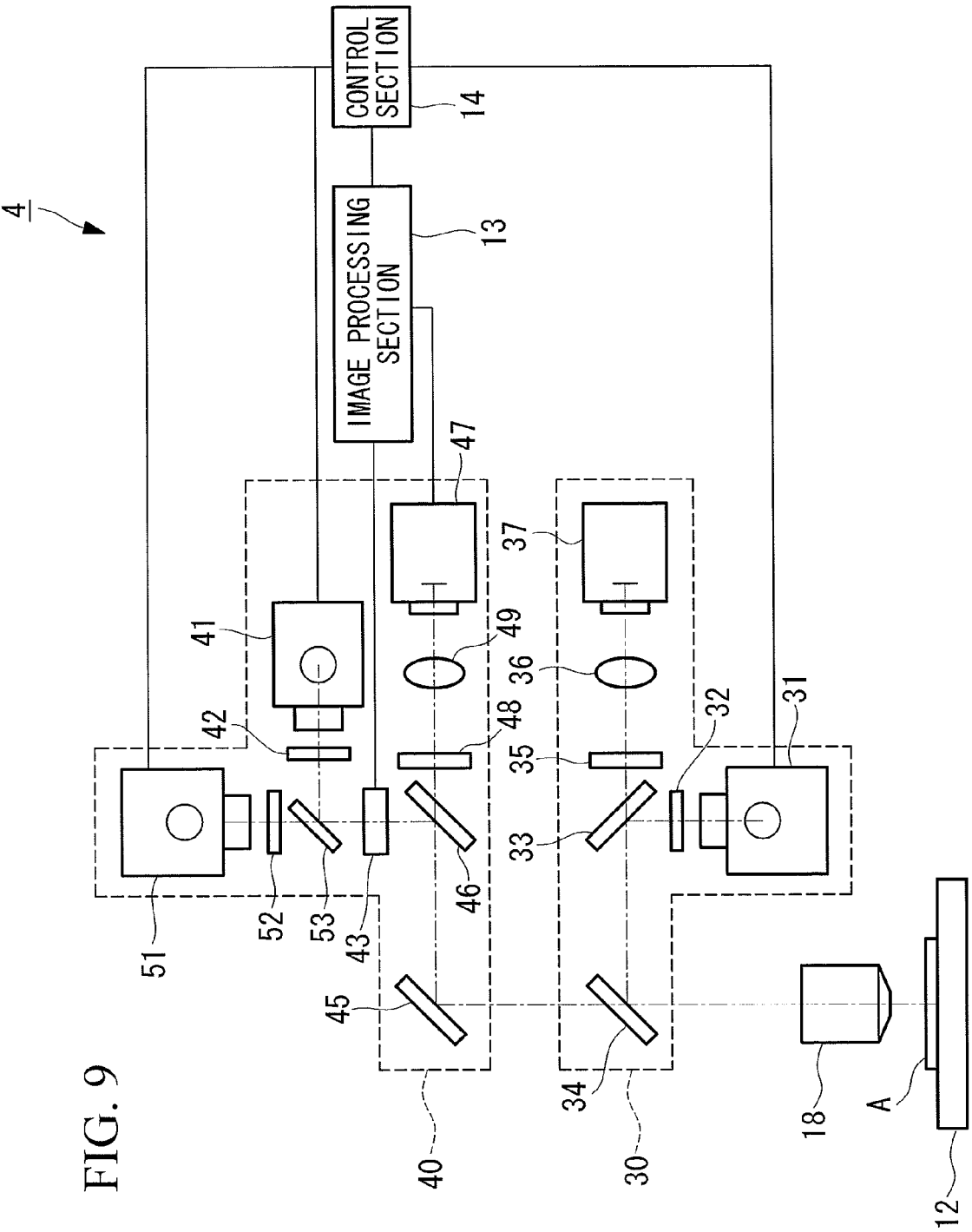
FIG. 9 is a diagram showing, in outline, the configuration of a microscope according to a second modification of the microscope shown in FIG. 7.

As shown in FIG. 9, the second optical system 40 is used to stimulate the stimulus target included in the specimen A and includes the second light source 41 that emits illumination light, the Ex filter (excitation filter) 42 that transmits light having a predetermined wavelength range, a third light source 51 that emits illumination light, an Ex filter (excitation filter) 52 that transmits light having a predetermined wavelength range, a dichroic mirror 53 that combines the light paths of the second light source 41 and the third light source 51, the deflecting device 43 that deflects the illumination light emitted from the second light source 41 and the third light source 51, the mirror 45 that reflects the illumination light deflected by the deflecting device 43, the dichroic mirror 46 that separates the illumination light and light from the specimen A, the Em filter (fluorescence filter) 48 that transmits light having a predetermined wavelength range, the imaging lens 49 that forms, on the second detector 47, an image of the light from the specimen A that has been transmitted through the Em filter 48, and the second detector (light detector) 47 that detects the light from the specimen A whose image has been formed by the imaging lens 49.

According to the microscope 4 of this modification, having the above-described configuration, it is possible to generate an image used to identify the positions of the stimulus target from the light detected by the second detector 47 and to generate an image of the specimen A in which the stimulus target has been stimulated from the light detected by the first detector 37; thus, the specimen A can be continuously observed at the same time as image processing being performed. Furthermore, it is possible to simultaneously emit light having the wavelength λ1, used to identify the positions of the stimulus target, from the third light source 51, light having the wavelength λ2, used to stimulate the stimulus target, from the second light source 41, and light having the wavelength λ3, used to acquire an image of the specimen A, from the first light source 31. Thus, even if the specimen A is considerably changed in position and shape, it is possible to observe the specimen A when a stimulus is given and to improve the accuracy of observation of the specimen A.

Third Modification

A third modification of the microscope 2 according to this embodiment will be described below with reference to FIG. 10.

Figure 10:
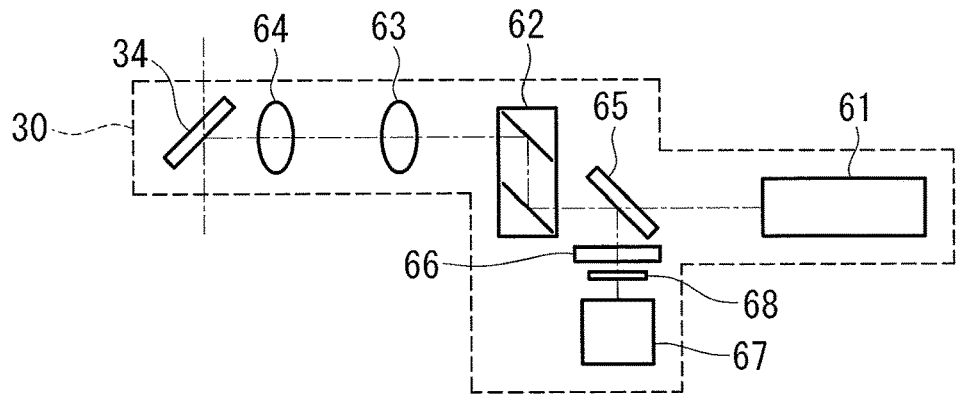
FIG. 10 is a diagram showing, in outline, the configuration of a first optical system according to a third modification of a first optical system shown in FIG. 7.

In this modification, as shown in FIG. 10, the first optical system 30 is used to perform scanning with laser light and includes a laser light source 61 that emits laser light, a galvanometer mirror 62 that performs scanning with the laser light emitted from the laser light source 61, a pupil projection lens 63 that projects the pupil of the laser light, an imaging lens 64 that forms an image of the laser light, the dichroic mirror 34 and a dichroic mirror 65 that separate illumination light and light from the specimen A, an Em filter (fluorescence filter) 66 that transmits light having a predetermined wavelength range, a detector (light detector) 67 that detects the light from the specimen A that has been transmitted through the Em filter 66, and a pinhole 68 that is provided between the Em filter 66 and the detector 67.

With the above-described configuration, it is possible to scan the specimen A with the laser light emitted from the laser light source 61 by operating the galvanometer mirror 62 and to generate an image of the specimen A by associating the scanning position with the intensity of the light from the specimen A that has been detected by the detector 67. Thus, the detector can be reduced in size.

Fourth Modification

A fourth modification of the microscope 2 according to this embodiment will be described below with reference to FIG. 11.

Figure 11:
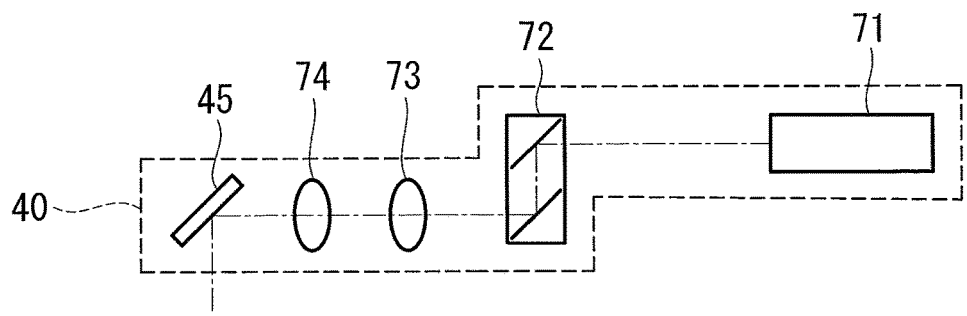
FIG. 11 is a diagram showing, in outline, the configuration of a second optical system according to a fourth modification of a second optical system shown in FIG. 7.

In this modification, as shown in FIG. 11, the second optical system 40 is used to perform scanning with laser light and includes a laser light source 71 that emits laser light, a galvanometer mirror (deflecting section) 72 that performs scanning with the laser light emitted from the laser light source 71, a pupil projection lens 73 that projects the pupil of the laser light, an imaging lens 74 that forms an image of the laser light, and the mirror 45 that reflects the laser light.

With the above-described configuration, an area of the specimen A to be irradiated with the laser light radiated through the objective lens 18 can be changed by operating the galvanometer mirror 72.

Fifth Modification

A fifth modification of the microscope 2 according to this embodiment will be described below with reference to FIG. 12.

Figure 12:
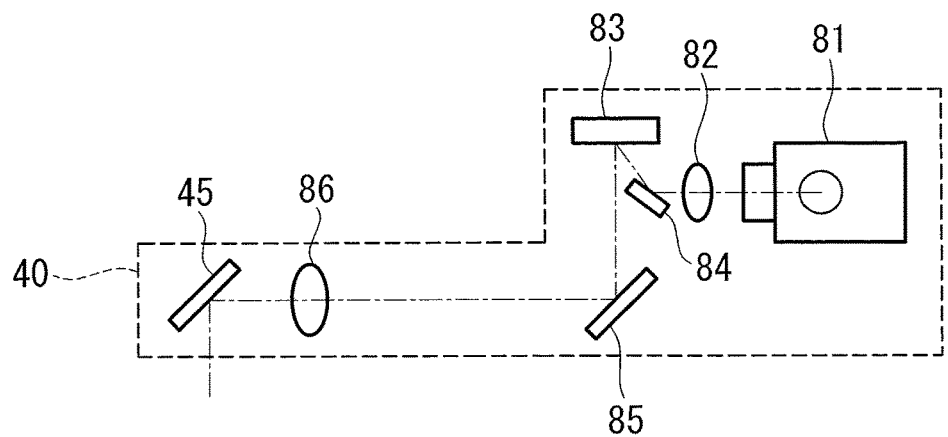
FIG. 12 is a diagram showing, in outline, the configuration of a second optical system according to a fifth modification of the second optical system shown in FIG. 7.

In this modification, as shown in FIG. 12, the second optical system 40 includes a laser light source 81 that emits laser light, a pupil projection lens 82 that projects the pupil of the laser light emitted from the laser light source 81, a mirror 84 that reflects the laser light toward a DMD 83, the DMD (deflecting section) 83 that selectively reflects part or all of the laser light, an imaging lens 86 that forms an image of the laser light, and the mirror 45 and a mirror 85 that reflect the laser light.

The DMD 83 is a microdevice array on which a plurality of microdevices that reflect or transmit the laser light emitted from the laser light source 81 are arrayed.

With the above-described configuration, by operating movable micromirrors (not shown) of the DMD 83 (turning them ON/OFF), it is possible to selectively reflect part or all of the laser light emitted from the laser light source 81 toward the mirror 85 to change the area of the specimen A to be irradiated with the laser light.

Third Embodiment

A third embodiment will be described below, in which a microscope according to one of the above-described embodiments is used in a microscope system that has a monitor and an input section. Here, a description will be given of an example in which the microscope 2 of the second embodiment is used.

Figure 13:
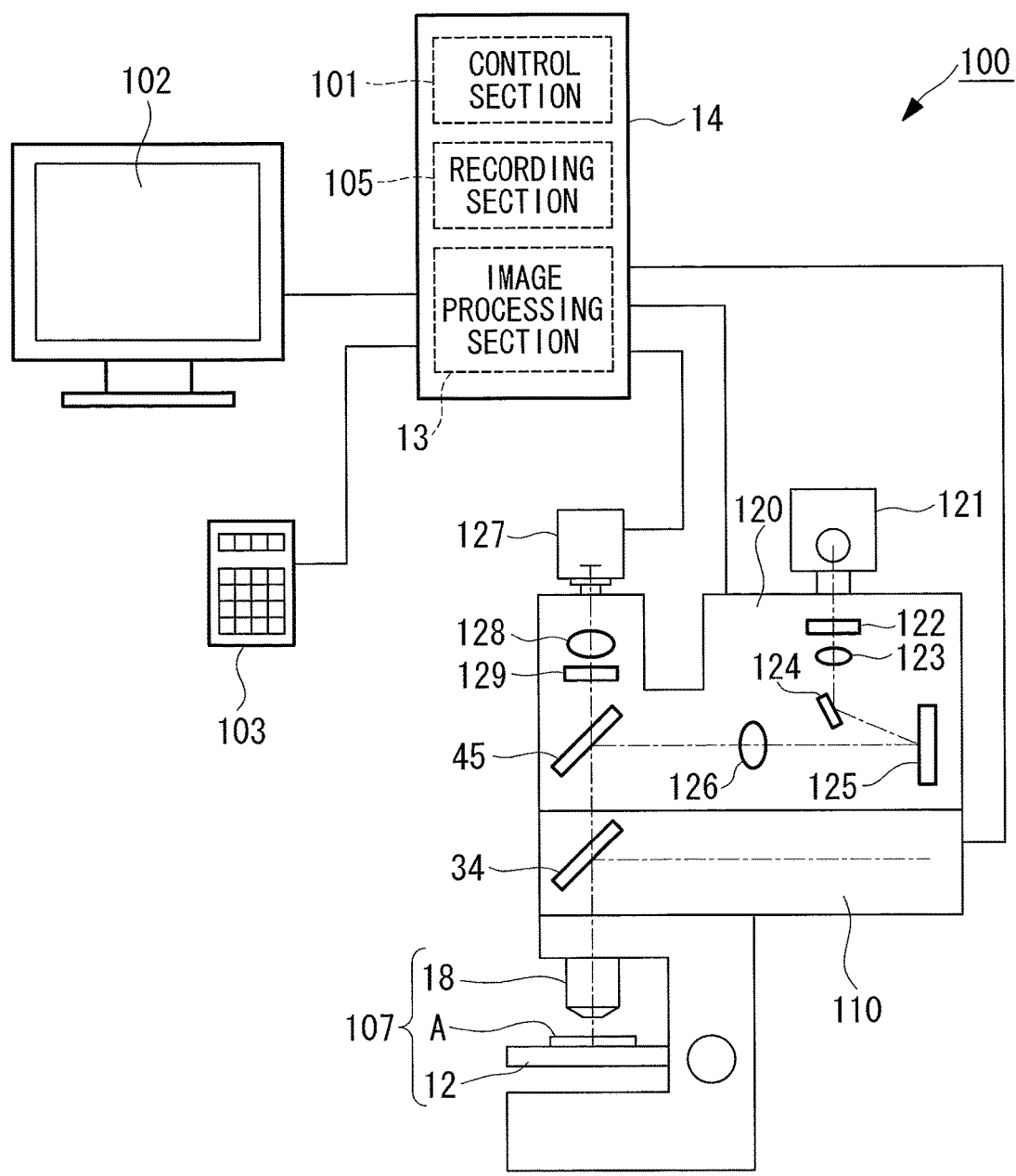
FIG. 13 is a diagram showing, in outline, the configuration of a microscope system according to a third embodiment of the present invention.

As shown in FIG. 13, a microscope system 100 of this embodiment includes a microscope main body unit 107, an observation unit 110 that is used to observe the specimen A, a light stimulation unit 120 that is used to stimulate a stimulus target included in the specimen A, a monitor 102 that displays an image of the specimen A acquired by the observation unit 110, an input section 103 that is used to input conditions for observing the specimen A, and a control unit 101 that controls these components.

The microscope main body unit 107 includes the stage 12 on which the specimen A is placed and the objective lens 18 that is disposed facing the specimen A.

The control unit 101 includes the image processing section (image generation section) 13 that generates an image from light coming from the specimen A, collected by the objective lens 18, a recording section 105 that records the image generated by the image processing section 13, and the control section 14 that controls the respective components.

Although components of the observation unit 110 are omitted in FIG. 13, the observation unit 110 has the same configuration as the first optical system 30 shown in FIGS. 7 to 10, for example.

The light stimulation unit 120 includes a second light source 121 that emits illumination light, an Ex filter (excitation filter) 122 that transmits light having a predetermined wavelength range, a condensing lens 123 that condenses the illumination light transmitted through the Ex filter 122, a mirror 124 that reflects the illumination light condensed by the condensing lens 123 toward a DMD 125, the DMD (deflecting section) 125 that selectively reflects part or all of the laser light, a pupil projection lens 126 that projects the pupil of the illumination light, a dichroic mirror 45 that separates the illumination light and light from the specimen A, an Em filter (fluorescence filter) 129 that transmits light having a predetermined wavelength range, an imaging lens 128 that forms, on a detector 127, an image of the light from the specimen A that has been transmitted through the Em filter 129, and the detector (light detector) 127 that detects the light from the specimen A whose image has been formed by the imaging lens 128.

According to the microscope system 100 of this embodiment, having the above-described configuration, since the microscope 2 of the second embodiment is included, it is possible to detect the positions of the stimulus target by using light having the wavelength λ1, to stimulate the stimulus target by using light having the wavelength λ2, and to acquire an image of the specimen A in which the stimulus target has been stimulated, by using light having the wavelength λ3. Thus, it is possible to change the stimulation positions in accordance with the positions and the shapes of the stimulus target included in the specimen A, to observe the specimen A immediately after stimulation, and to improve the accuracy of observation of the specimen A.

Note that a description has been given of an example in which the microscope 2 of the second embodiment is used in the microscope system 100 of this embodiment; however, the microscope 1 of the first embodiment may be used instead.

Modification

Figure 14:
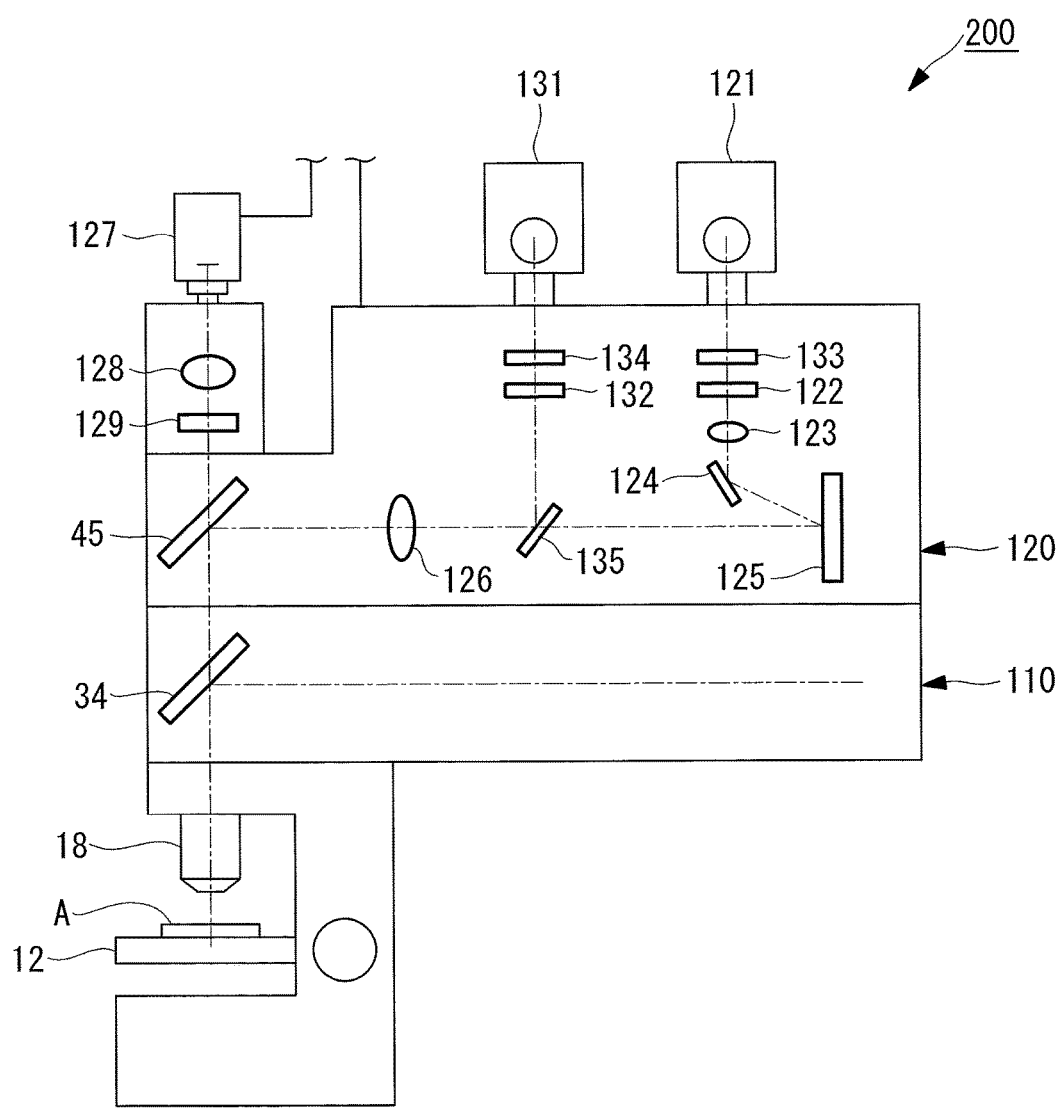
FIG. 14 is a diagram showing, in outline, the configuration of a microscope system according to a modification of the microscope system shown in FIG. 13.

A modification of the microscope system 100 according to this embodiment will be described below with reference to FIG. 14.

In a microscope system 200 of this modification, the light stimulation unit 120 includes, in addition to the components shown in FIG. 13, a third light source 131 that emits illumination light, an Ex filter (excitation filter) 132 that transmits light having a predetermined wavelength range, a shutter 133 provided on the optical axis of the second light source 121, a shutter 134 provided on the optical axis of the third light source 131, and a dichroic mirror 135 that combines the light path of the second light source 121 and the light path of the third light source 131.

The shutters 133 and 134 are opened and closed by drive mechanisms (not shown) to switch illumination light from the second light source 121 and illumination light from the third light source 131, to irradiate the specimen A.

According to the microscope system 200 of this modification, since the three light sources are included, it is possible to simultaneously emit light having the wavelength λ1, used to identify the positions of the stimulus target, light having the wavelength λ2, used to stimulate the stimulus target, and light having the wavelength λ3, used to acquire an image of the specimen A. Thus, even if the specimen A is considerably changed in position and shape, it is possible to observe the specimen A when a stimulus is given and to improve the accuracy of observation of the specimen A.

Although a detailed description has been given of the respective embodiments of the present invention with reference to the drawings, the specific configuration is not limited to the embodiments, and design changes made without departing from the scope of the present invention are also encompassed. For example, the present invention is not limited to the above-described embodiments and modifications and may be applied to an embodiment obtained by appropriately combining these embodiments and modifications.

A specimen
1, 2, 3, 4 microscope
10 illumination optical system
11 light source
12 stage
13 image processing section (image generation section)
14 control section
15 deflecting device (deflecting section)
17 dichroic mirror
18 objective lens
20 observation optical system
25 detector (light detector)
30 first optical system
31 first light source
33, 34 dichroic mirror
37 first detector (light detector)
40 second optical system
41 second light source
43 deflecting device (deflecting section)
47 second detector (light detector)
51 third light source
62, 72 galvanometer mirror
83 DMD
100, 200 microscope system
101 control unit
102 monitor
103 input section
105 recording section
107 microscope main body unit
110 observation unit
120 light stimulation unit

What is claimed is:

1. An observation method comprising:
   (1) irradiating a specimen with light having a first wavelength to excite a fluorescent substance within a target analyte and acquiring a fluorescence image of the specimen,
   wherein the fluorescent substance has been bound to or is expressed within the target analyte prior to irradiating with the first wavelength,
   (2) obtaining a position of the fluorescent substance in the fluorescence image, thereby providing an area of the specimen containing the target analyte,
   (3) irradiating the area of the specimen containing the target analyte with a second wavelength, wherein said irradiating causes a photochemical reaction in the target analyte, thereby stimulating the target analyte,
   (4) irradiating the area of the specimen containing the target analyte with a third wavelength to detect a second target object that is different from the target analyte of the specimen, and
   (5) acquiring a final image of the specimen that includes the stimulated target analyte and the second target object that is different from the target analyte,
   wherein the method is performed using an observation apparatus comprising (i) a first optical system and a second optical system, the first optical system comprising a first light source that selectively emits the first wavelength and the third wavelength, and a light detector, (ii) the second optical system comprising a second light source that emits the second wavelength, and a deflector that deflects the second wavelength, and (iii) a controller that controls the first light source in order to perform the irradiating step (1) and the irradiating step (4), and controls the second light source in order to perform the irradiating step (3).

2. An observation method comprising:
   (1) irradiating a specimen with light having a first wavelength to excite a fluorescent substance and acquiring a fluorescence image of the specimen, wherein the fluorescent substance has been bound to or is expressed within the target analyte prior to irradiating with the first wavelength, (2) obtaining a position of the fluorescent substance in the fluorescence image, thereby providing an area of the specimen containing the target analyte, (3) irradiating the area of the specimen containing the target analyte with a second wavelength, wherein said irradiating causes a photochemical reaction in the target analyte, thereby stimulating the target analyte, (4) irradiating the area of the specimen containing the target analyte with a third wavelength to detect a second target object that is different from the target analyte of the specimen, and (5) acquiring a final image of the specimen that includes the stimulated target analyte and the second target object that is different from the target analyte, wherein the method is performed using an observation apparatus comprising (i) a first optical system comprising a first light source that emits the third wavelength and a first light detector, (ii) a second optical system comprising a second light source that emits the second wavelength, a third light source that emits the first wavelength, a deflector that deflects the second wavelength, and a second light detector, and (iii) a controller that controls the third light source in order to perform the irradiating step (1), controls the second light source in order to perform the irradiating step (3), and controls the first light source to perform the irradiating step (4).

3. The observation method of claim 1, wherein the first optical system further comprises a galvanometer mirror.

4. The observation method of claim 1, wherein the deflector of the second optical system is a digital mirror device on which a plurality of movable mirrors are arrayed.

5. The observation method of claim 1, further comprising recording (i) the fluorescence image acquired at step (1), and (ii) the final image of the specimen acquired at step (5), in a recording section of the observation apparatus, wherein the recording section is a memory.

6. The observation method of claim 1, wherein the deflector of the second optical system is a galvanometer mirror.

7. The observation method of claim 1, wherein the specimen is a cranial nerve specimen, the target analyte is channelrhodopsin, and the second target object is calcium.

8. The observation method of claim 2, wherein the specimen is a cranial nerve specimen, the target analyte is channelrhodopsin, and the second target object is calcium.

* * * * *